(12) United States Patent
Otten, III et al.

(10) Patent No.: US 7,104,649 B2
(45) Date of Patent: *Sep. 12, 2006

(54) WAVEFRONT CHARACTERIZATION OF CORNEAS

(75) Inventors: Leonard John Otten, III, Placitas, NM (US); Gavin R. G. Erry, Gt Malvern (GB); Simon C. Woods, Cheltenham (GB); Paul Harrison, Wellington Heath (GB)

(73) Assignee: Kestrel Corporation, Albuquerque, NM (US)

( * ) Notice: Subject to any disclaimer, the term of this patent is extended or adjusted under 35 U.S.C. 154(b) by 848 days.

This patent is subject to a terminal disclaimer.

(21) Appl. No.: 10/115,355

(22) Filed: Apr. 2, 2002

(65) Prior Publication Data

US 2002/0151801 A1 Oct. 17, 2002

Related U.S. Application Data

(60) Continuation of application No. 09/895,309, filed on Jun. 29, 2001, which is a division of application No. 09/693,076, filed on Oct. 20, 2000, now Pat. No. 6,286,959.

(51) Int. Cl.
*A61B 3/10* (2006.01)

(52) U.S. Cl. ...................................................... 351/212
(58) Field of Classification Search .................. 351/205, 351/211, 212, 219, 221, 246, 247; 606/4, 606/5; 356/124
See application file for complete search history.

(56) References Cited

U.S. PATENT DOCUMENTS 4,695,536 A  9/1987  Lindstrom et al.
6,095,651 A * 8/2000  Williams et al. ............. 351/246
6,271,915 B1 * 8/2001  Frey et al. ................... 356/124

FOREIGN PATENT DOCUMENTS

WO    WO 99/46768    9/1999

OTHER PUBLICATIONS

*Laser Wavefront Sensing Using the Intensity Transport Equation*, Simon Woods, Paul M. Blanchard and Alan H. Greenaway, Proceedings of the 2nd International Workshop on Adaptive Optics for Indusry and Medicine, pp. 260–265 Jul. 12–16, 1999.

(Continued)

Primary Examiner—George Manuel
(74) Attorney, Agent, or Firm—DeWitt M. Morgan

(57) ABSTRACT

Apparatus for determining if a cornea (whether in vitro or in vivo) has been modified (either surgically or otherwise). The method includes the steps of: passing a beam of collimated light a (either coherent or incoherent) through the cornea to produce a distorted wavefront; determining the characteristics of the distorted wavefront; and analyzing the distorted wavefront for characteristics that identify the presence of a modification. The analysis of the distorted wavefront can be for the presence of higher order aberrations, or Gausian characteristics which are indicative of modifications. More particularly, the method includes the steps of providing an optical system that has a pupil plane and an image plane at a detector; positioning the cornea in the pupil plane; passing a collimated beam of light through the cornea to produce at least two images in the image plane; determining the characteristics of the distorted wavefront; and analyzing the distorted wavefront for characteristics that identify the presence of a modification. The apparatus includes: a source of collimated light: an optical system including a distorted grating and an imaging lens (which have a pupil plane, first and second virtual planes, and an image plane); structure for positioning the cornea in the pupil plane; and a computer. The structure for positioning the cornea (which is immersed in a suitable storage fluid) includes first and second plano/plano lenses. The first and second plano lens, which are substantially and perpendicular to and centered with respect to the axis, have less than $\lambda/10$ total distortions.

24 Claims, 18 Drawing Sheets

OTHER PUBLICATIONS

*Multi–Plane Imaging With a Distorted Diffraction Grating*, P.M. Blancard and A. H. Greenaway, *Proceedings of the 2nd International Workshop on Adaptive Optics for Indusry and Medicine*, pp. 296–301, Jul. 12–16, 1999.

3–D Cataract Imaging System, L.J. Otten, P. Soliz, A. Greenaway, P. Blanchard, G. Ogawa, and I. MacMakin.

Optisol–GS, Corneal Viewing Chamber, Bausch & Lomb Surgical product brochure, 1998.

* cited by examiner

WAVEFRONT CHARACTERIZATION OF CORNEAS

RELATED U.S. APPLICATION DATA

This application is a continuation of application Ser. No. 09/895,309 filed Jun. 29, 2001 which, in turn, is a divisional of application Ser. No. 09/693,076, filed on Oct. 20, 2000, now U.S. Pat. No. 6,286,959 B1.

FIELD OF THE INVENTION

This invention relates to the use of wavefront sensing to determine whether or not a cornea has been altered (due to corrective surgery, or accident). More specifically, the present invention relates to the use of wavefront sensing using a distorted defraction grating to identify corneas (whether in vitro or in vivo) that have been surgically modified (e.g., radical keratotomy (RK), excimer laser photorefractive keratectomy (PRK), laser-assisted in situ keratomileusis (LASIK) and automated lamellar keratoplasty (ALK)).

BACKGROUND OF THE INVENTION

In the United States about 40,000 corneal transplant operations are performed each year. While success of such surgery may depend upon a number of other factors, one factor that always has an effect on the outcome is the condition of the donor cornea. In the United States, a donor cornea must be transplanted within 7 days of harvesting. Outside the United States donor corneas may be used up to 14 days after harvesting. Additionally, it is essential to use only corneas which have not been modified (e.g., the subject of photorefractive surgery).

The growth of refractive surgery over the last five years has been dramatic. In the August 2000 issue of Archives of Ophthalmology, P. J. McDonnell, M.D. states that this year alone over 1,500,000 refractive procedures will be performed. As beneficial as these procedures are, the individual corneas are permanently altered, which makes them unsuitable for corneal transplanting.

The increase in refraction surgery increases the likelihood that a modified cornea will be harvested for transplant purposes. Unfortunately, it is generally not possible to conclusively tell, either visually or under a microscope, whether such a donor cornea has been subjected to a surgical procedure or otherwise altered.

Even when properly stored in a container (e.g., a Chiron Ophtholmics cornea container) filled with Optisol® or another appropriate solution, a donated cornea changes optically in the 14 day time period referenced above. The interior starts to develop optical scatter sources and the optical power of the cornea changes. The scatter resources manifest themselves as randomly distributed optical aberrations which increase over time. It is believed that this is caused by the cells of the harvested cornea not being able to reject waste material. The change in optical power is believed to be caused by an overall relaxation of the tissue. Regardless of the cause, the net result is that these aberrations produce scintillation and static aberrations when a beam of light is passed through a donated cornea.

PCT/GB99/00658 (International Publication No. WO 99/467768), based on applications filed in Great Britain on Mar. 10, 1998 and Dec. 23, 1998, discloses a three dimensional imaging system including a lens and a distorted diffraction grating which images objects located at different distances from the grating simultaneously and spatially separated in a single image plane. The grating is distorted according to a quadratic function so as to cause the images to be formed under different focus conditions. It is stated that the system is useful for simultaneously imaging multiple layers within a three dimensional object field, and has applicability in a number of fields including optical information storage, imaging short-time scale phenomena, microscopy, imaging three dimensional object structures, passive ranging, laser beam profiling, wavefront analysis, and millimeter wave optics. The ability to make wavefront measurements is not disclosed or claimed.

P. M. Blanchard et al., "Multi-Plane Imaging With a Distorted Grating," Proceedings of the 2nd International Workshop on Adaptive Optics for Industry and Medicine, World Scientific, pp. 296–301, Jul. 12–16, 1999, describe a technique for simultaneously imaging multiple layers within an object field onto the detector plane of a single detector. The authors, who are the named inventors in PCT/GB99/00658, state that the imaging of multiple layers within an object field is "useful in many applications including microscopy, medical imaging and data storage." (See page 296.) The apparatus includes the use of a binary diffraction grating in which the lines are distorted such at each different level of defocus is associated with each diffraction order. When such a grating is placed in close proximity to a lens, the grating creates multiple foci of the image. This multifoci effect enables the imaging of multiple object planes onto a single image plane.

L. J. Otten et al. "3-D Cataract Imaging System," Proceedings of the 2nd International Workshop in Adaptive Optics for Industry and Medicine, World Scientific, pp. 51–56, describe optics and an associated diagnostic system for volumetric, in vivo imaging of the human lens to characterize or grade cataracts. The described method and apparatus are based on the use of a distorted grating (of the type disclosed in PCT/GB99/00658 and the Blanchard et al. paper, supra) in conjunction with a focusing lens and a re-imaging lens. (See FIG. 1 of this reference.) The quadratic phase shift, introduced by the grating, leads to a different degree of defocus in all diffraction orders, which produces a series of images of different layers of the cataract, each with different defocus conditions, simultaneously and side-by-side on the detector. Thus, in-focus images of different object planes are produced.

Analysis of the optical images referenced above requires the use of the Intensity Transport Equation (I.T.E.) and the employment of a Green's function to produce a wavefront map. S. Woods, P. M. Blanchard and A. H. Greenaway, "Laser Wavefront Sensing Using the Intensity Transport Equation," Proceedings of the 2nd International Workshop on Adaptive Optics for Industry and Medicine, World Scientific, pp. 260–265, Jul. 12–16, 1999, describe both the I.T.E. and a Green's function solution thereto in conjunction with laser wavefront sensing.

OBJECT OF THE INVENTION

It is an object of the present invention to determine, with wavefront sensing, whether or not a cornea has been altered (either deliberately or accidentally).

It is another object of the present invention to determine, with the use of wavefront sensing using a distorted grating, those donor corneas that have been modified by surgery or other methods.

It is another object of the present invention to provide a simple optical system (particularly including a light source, an imaging lens, a distorted grating and a data camera) to form, in the detector plane, images from which wavefront aberrations in the cornea can be derived. The beam of light that passes through a cornea (located in the pupil plane) and two virtual planes on opposite sides of and equidistant from such pupil plane.

It is an additional object of the present invention to provide a holder for a donor cornea which does not mask optical data from such cornea.

It is yet another object of the present invention to provide a holder for a donor cornea that has optical windows that are substantially free of distortion which would mask corneal optical data.

It is yet still another object of the present invention in which the optical windows have less than $\lambda/10$ distortions.

These and other objects will be apparent from the description which follows.

SUMMARY OF THE INVENTION

A method of determining if a cornea (whether in vitro or in vivo) has been modified (either surgically or otherwise). The method includes the steps of: passing a beam of collimated light a (either coherent or incoherent) through the cornea to produce a distorted wavefront; determining the characteristics of the distorted wavefront; and analyzing the distorted wavefront for characteristics that identify the presence of a modification. The analysis of the distorted wavefront can be for the presence of higher order aberrations, or Gausian characteristics which are indicative of modifications. More particularly, the method includes the steps of providing an optical system that has a pupil plane and an image plane at a detector; positioning the cornea in the pupil plane; passing a collimated beam of light through the cornea to produce at least two images in the image plane; determining the characteristics of the distorted wavefront; and analyzing the distorted wavefront for characteristics that identify the presence of a modification.

The apparatus for determining whether a cornea has been surgically modified includes: a source of collimated light, an optical system including a distorted grating and an imaging lens (which have a pupil plane, first and second virtual planes, and an image plane); structure for positioning the cornea in the pupil plane; means for recording the images of the first and second virtual planes; means for determining from the first and second images the distorted wavefront; and means for analyzing said wavefront for characteristics indicative of modified corneas. The first and second virtual planes are on opposite sides of and equally spaced from said pupil plane.

The structure for positioning the cornea (which is immersed in a suitable storage fluid) is a container which includes: a housing having first and second ends; structure positioned within the housing for supporting the perimeter of the cornea; a first plano/plano lens for closing the first end of the housing; and a cap for closing the second end of the housing. The cornea support is substantially symmetrical with respect to an optical axis. The first plano/plano lens is substantially perpendicular to the optical axis. Finally, the cap includes a second plano/plano lens which is substantially parallel to the first plano lens. The first and second plano/plano lens, which are substantially centered with respect to the axis, have less than $\lambda/10$ total distortions. The support structure includes a cage and a pedestal with the cage being supported by the pedestal. Preferably, the cage and pedestal are integrally formed with the housing. Finally, the cap has a top portion and a skirt which axially inwardly spaces the second lens from the top portion to create an annular area where air will collect when the container is holding a cornea and fluid, so that air will not interfere with a beam of light passing through the first and second plano/plano lenses and cornea.

BRIEF DESCRIPTION OF THE DRAWINGS

FIG. 1A is the front view of the distorted grating used in the instrumentation to characterize corneas;

FIG. 1B is the front view of the detector plane of the detector of the instrumentation to characterize corneas, and the images in such plane;

DESCRIPTION OF THE PREFERRED EMBODIMENT

Figure 1:
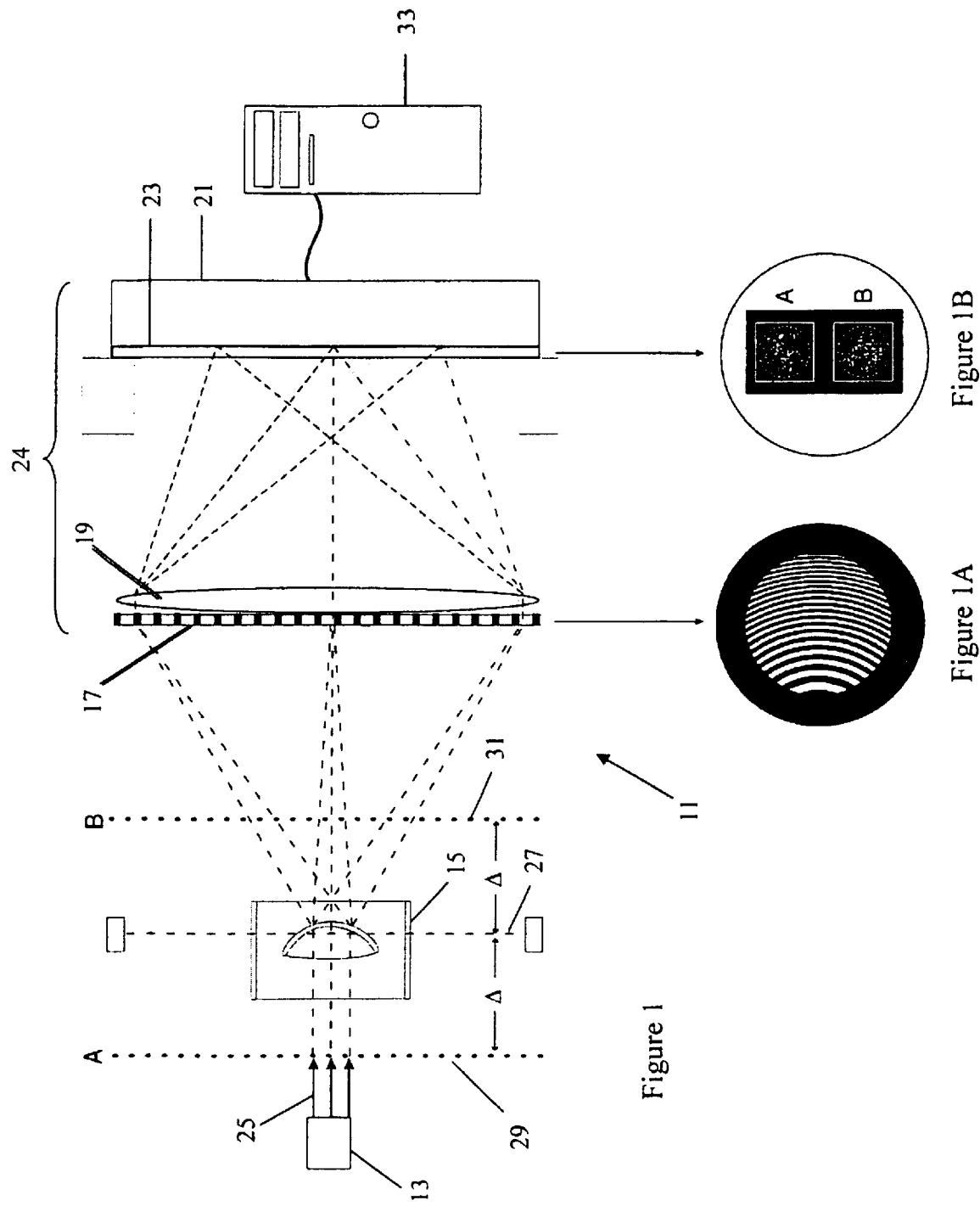
FIG. 1 is a schematic of the optical system of the instrument to characterize donor corneas.

With reference to FIG. 1, the apparatus 11 for determining whether an in vitro cornea has been modified (either surgically or otherwise) includes a source of collimated coherent light 13, a cornea container 15, a distorted diffraction grating 17, a high quality imaging lens (or lens set) 19, and a detector 21 (either film or electronic) having a detector plane 23. (Grating 17, lens 19 and detector 21 are sometimes referred to as wavefront sensor 24.) Apparatus 11 also includes a beam path 25, a pupil plane 27, first virtual plane 29, second virtual plane 31, and a computer 33. Computer 33 is connected to detector 21, via a data acquisition device such as a frame grabber (located within the computer housing). Computer 33 stores the images form detector 21, determines the wavefront from the stored images, and analyzes the wavefront for the characteristics that identify an altered cornea (e.g. compares the wavefronts to a stored norm). The representation of the virtual planes between source 13 and sensor 24 is for convenience only. In the preferred embodiment they are 73 cm on either side of pupil plane 27. Source 13 is a coherent laser such as a 633 nm HeNe laser. As those skilled in the art will appreciate non-coherent sources, such as spectrally band filtered white light, could also be used.

With grating 17 in close proximity to lens 19 (typically these two elements would, in fact, be in contact with each other along beam path 25), the 0, +1 and −1 diffraction orders of grating 17 image pupil plane 27, virtual object plane 29 and virtual object plane 31 are projected onto detector plane 23. The higher order diffraction orders are cut off by an appropriately placed field stop so as not to contaminate the image of the 0 and +1 and −1 orders. Further, with the zero order being an image of the pupil plane 27, the images in the +1 and −1 diffraction orders correspond to virtual image planes equidistant from and an opposite sides of pupil plane 27. The grating is distorted according to, $$\Delta_x(x, y) \approx \frac{W_{20} d}{\lambda R^2}(x^2 + y^2)$$

where $\lambda$ is the optical wavelength, x and y are Cartesian co-ordinates with an origin on the optical axis and R is the radius of the grating aperture which is centered on the optical axis. The parameter $W_{20}$ defines the defocusing power of the gratings, and is the standard coefficient of the defocus equivalent on the extra pathlength introduced at the edge of the aperature, in this case for the wavefront diffracted into the +1 order. The phase change ($\emptyset_m$) imposed on the wavefront diffracted into each order m is given by, $$\varphi_m(x, y) = m \frac{2\pi W_{20}}{\lambda R^2}(x^2 + y^2)$$

Figure 2:
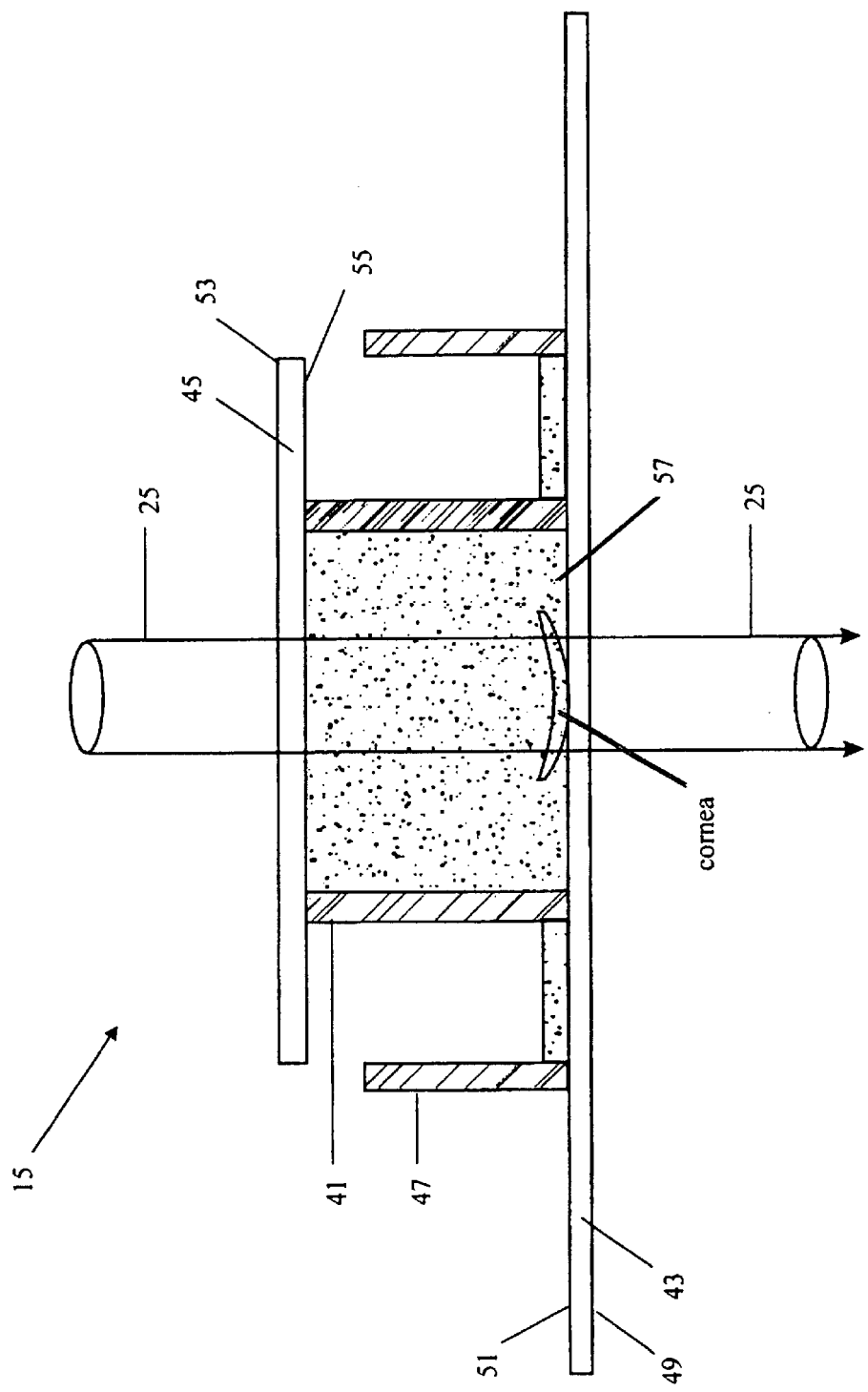
FIG. 2 is a cross-section view of an optical cornea container of the present invention.

The various containers in which donor corneas are stored are unusable for optical diagnostics. The aberrations produced by the walls of such containers mask the aberrations exhibited by corneas both unaltered and altered. With reference to FIG. 2, optical cornea container 15 includes cylindrical housing 41, first optical window 43, second optical window 45, and fluid containment ring 47. Housing 41 and ring 47 are concentric rings, both bonded to optical window 43. Window 43 is a plano/plano lens having surfaces 49, 51 which are substantially concentric with respect to beam path 25 and substantially perpendicular thereto. Similarly, window 45 is a plano/plano lens having surfaces 53, 55 which are also substantially concentric with and substantially perpendicular to beam path 25. Collectively, windows 43 and 45, including surfaces 49, 51 and 53, 55 have total aberrations of less than $\lambda/10$. In operation, cavity 57 is filled with Optisol®, or another solution suitable for the storage of donor corneas, to the top of housing 41 so that the meniscus causes such fluid to slightly over fill cavity 57. Window 45 is then slid over housing 41 without trapping any air in cavity 57. Excess fluid is collected between housing 41 and ring 47.

Figure 3:
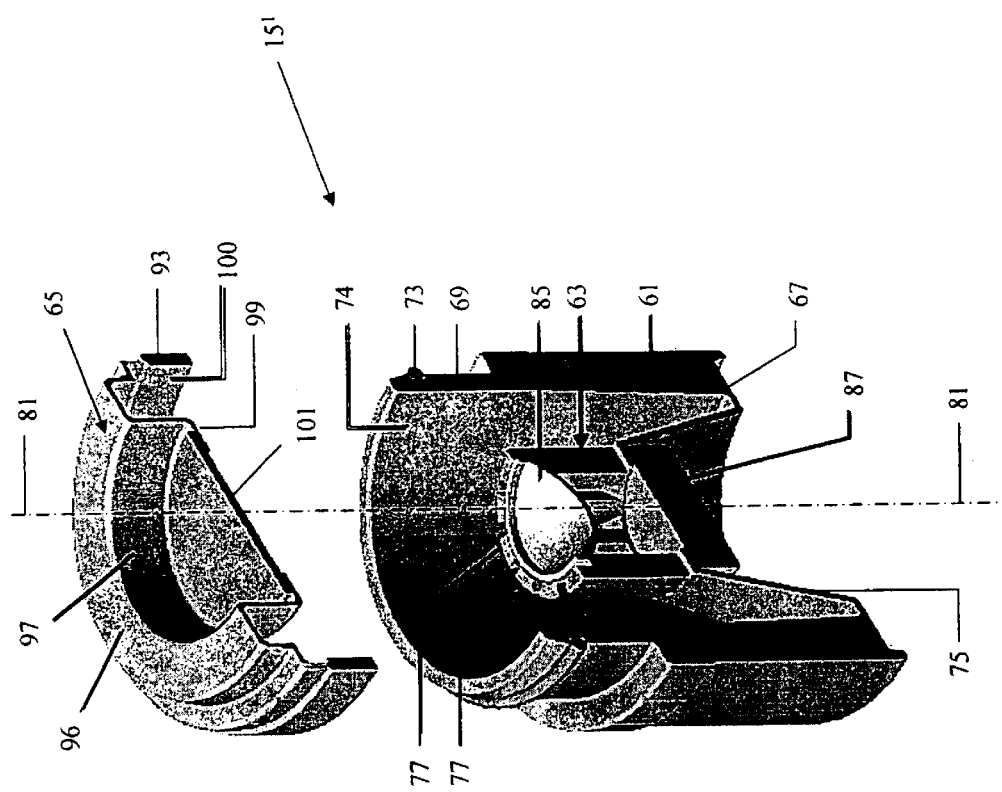
FIG. 3 is a cross-sectional, perspective view of an improved cornea container of the present invention.
Figure 4:
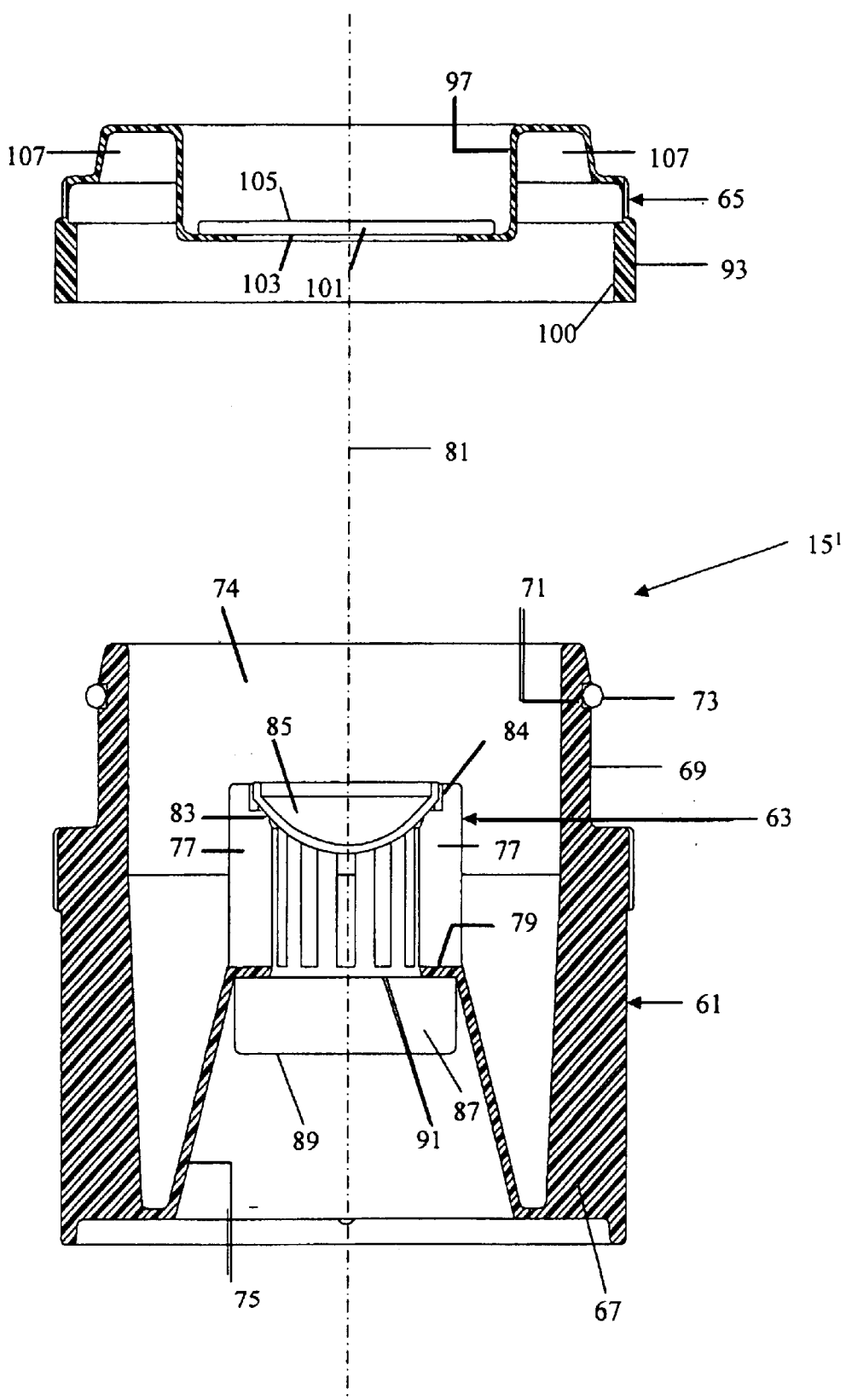
FIG. 4 is a cross-sectional view of the improved optical cornea container of FIG. 3 in the open position.

With reference to FIGS. 3 and 4, improved cornea container 15[1] includes a cylindrical body portion 61, a cornea support cage portion 63, and a cap portion 65. Body portion includes a bottom surface 67, an upper skirt portion 69 having a groove 71 therein for supporting an o-ring seal 73 and threads (not shown), and a cavity 74. Body portion 61 also includes a conical shaped skirt 75 integral with bottom surface 67 for centrally positioning cage portion 63 within body portion 61 as illustrated in FIGS. 3 and 4. Cage portion 63 includes a plurality of fingers 77, which are supported by ring portion 79 of skirt 75 in a cylindrical pattern concentric with axis 81. As best illustrated in FIG. 4, the free ends of fingers 77 include, inter alia, an inwardly sloping bevel 83 and notch 84 for supporting a donor cornea, such as illustrated at 85. Finally, body portion 61 includes a plano/plano lens 87 secured to ring portion 79. Lens 87 has parallel plano surfaces 89 and 91 which are substantially centered with respect to axis 81 and substantially perpendicular thereto. Cap portion 65 includes a skirt portion 93, a shoulder 95 which seats against 73, a top portion 96, and an inner skirt portion 97 having a circumferential lip 99. Inner surface 100 includes threads (not shown) which mate with the threads (also not shown) on skirt 69. Secured to lip 99 is a second plano/plano lens 101 having plano parallel surfaces 103 and 105. When cornea container 15[1] is closed, with seal 73 received in circumferential recess 95, surfaces 103 and 105 are substantially centered with respect to to axis 81 and substantially perpendicular thereto. Collectively, the aberrations in lenses 87 and 101, including surfaces 89, 91, 103 and 105, have a total aberration of less than $\lambda/10$.

Figure 4A:
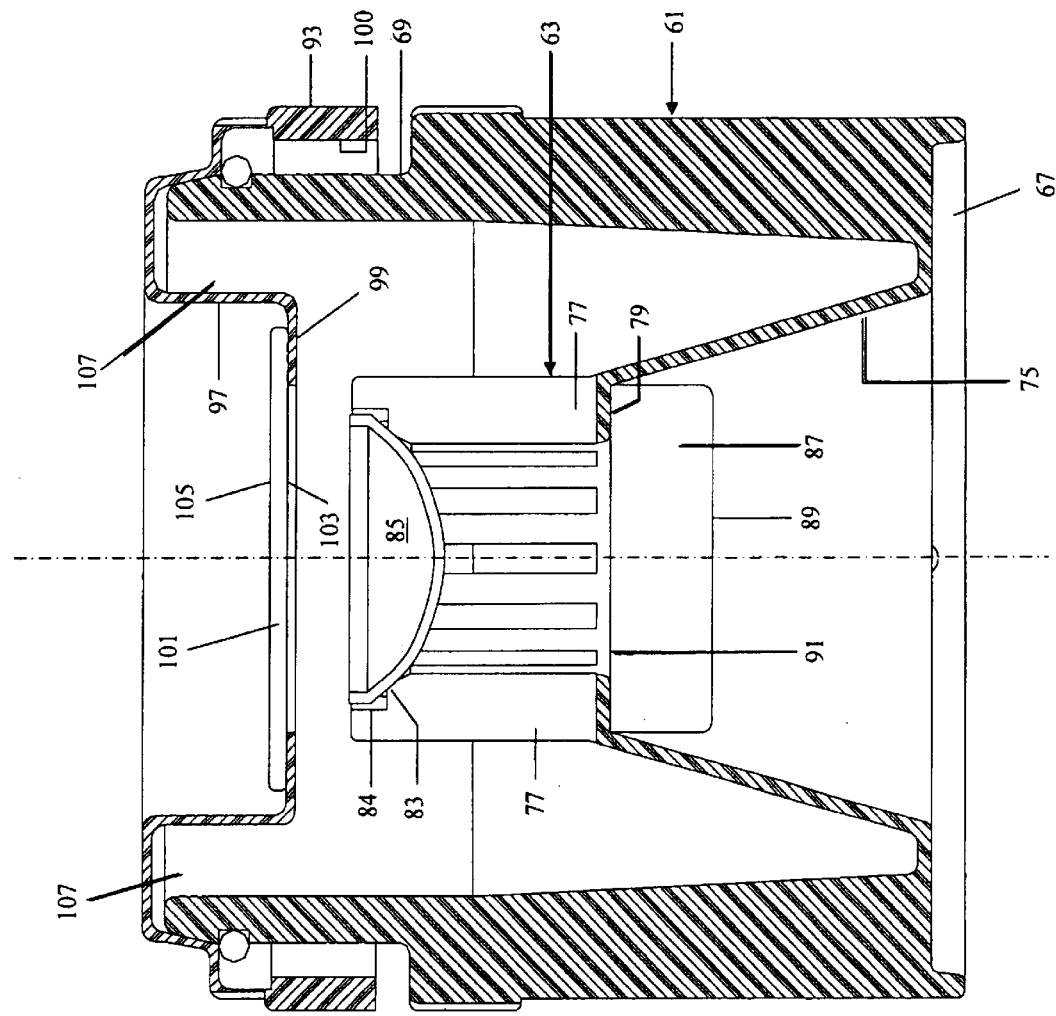
FIG. 4A is a cross sectional view of the improved optical cornea container of FIG. 3 in the closed position.

In operation, donor cornea 85 is placed in cage 63, with a portion of the convex surface thereof in contact with bevels 83 and the perimeter received within notches 84. In this position, donor cornea is substantially centered about axis 81. Cavity 74 is then filled with a suitable storage fluid and capped by screwing on cap 65. As can be seen from FIG. 4A, because inner skirt portion 97 projects inwardly, closure of cap 65 will force excess fluid out of cavity 74. In the event that there is any under filling of cavity 74, any air which might be trapped in cavity 74 is collected in annular area 107 (outside of the beam path).

Figure 5:
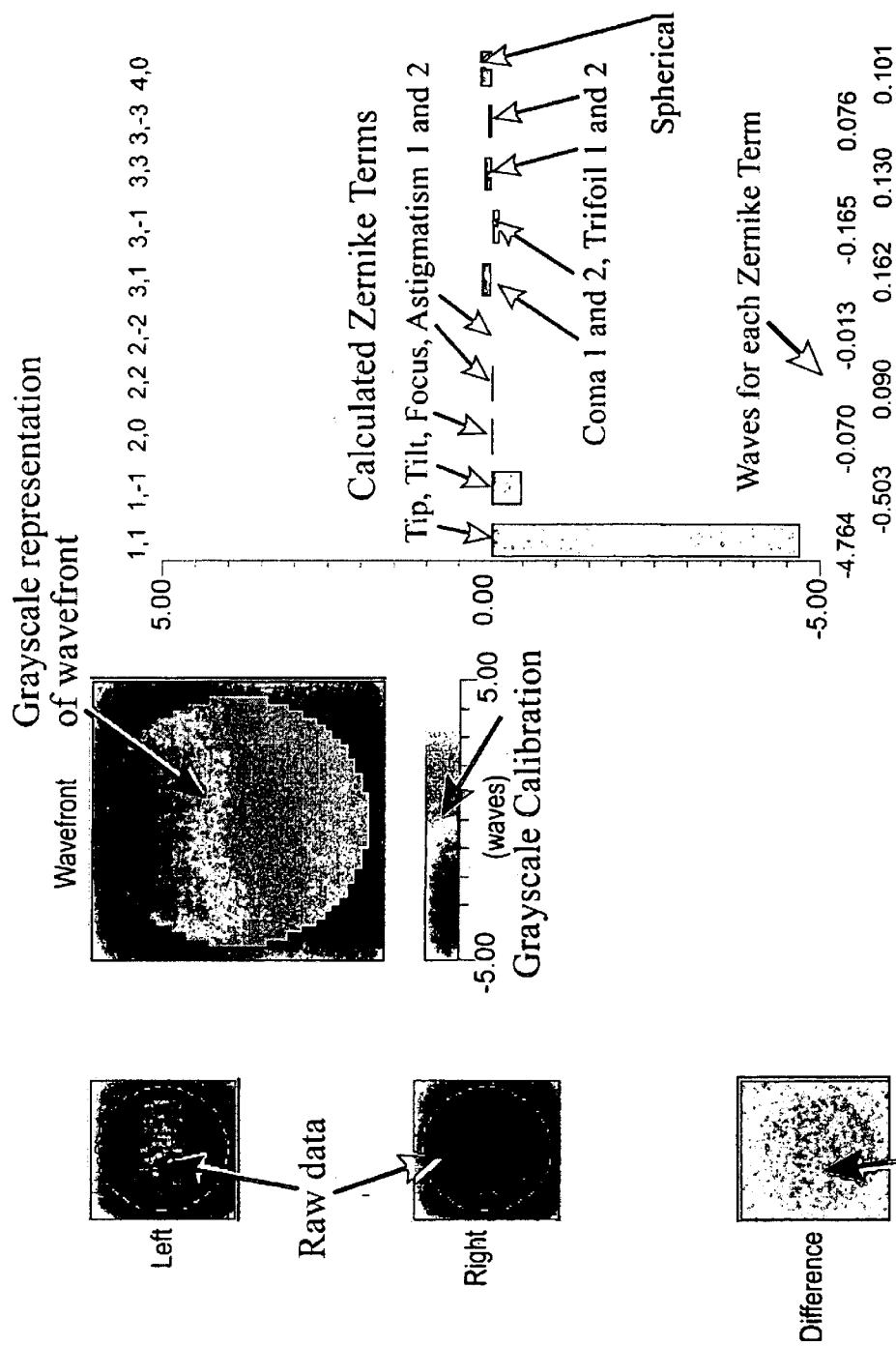
FIG. 5 is a diagram showing the baseline date of the system of FIG. 1, with no cornea or container.

With nothing in pupil plane 27 of apparatus 11 (e.g., cornea container 15 removed) and source 13 present, the images recorded on detector plane 23 are as illustrated in FIG. 1B. Data was collected without any disturbances (i.e., no cornea container, cornea storage solution, or cornea) to determine the residual errors in the optics and, thus, establish the base line for instrument 11. With reference to FIG. 5, the raw images as recorded by detector 21 are shown along with the reduced Zernike terms, annotated to show where the various types of data are located in the figure. All the data are taken using a 633 nanometer HeNe laser as the illumination source. Most of the error is tip and tilt, which is the result of not accurately aligning wavefront sensor 24 and for not accurately accounting for where the distorted grating images were actually placed on detector plane 23. These two terms can be made equal to zero by: (1) subtracting them in the analysis of the wavefront to accommodate images that are not exactly centered on the same line; or (2) a more precise alignment of wavefront sensor 24. The other aberrations (e.g. focus) are seen to be small, on the order of or less than 0.1λ. All the baseline aberrations, including tip and tilt, can be subtracted from the cornea data.

Figure 6:
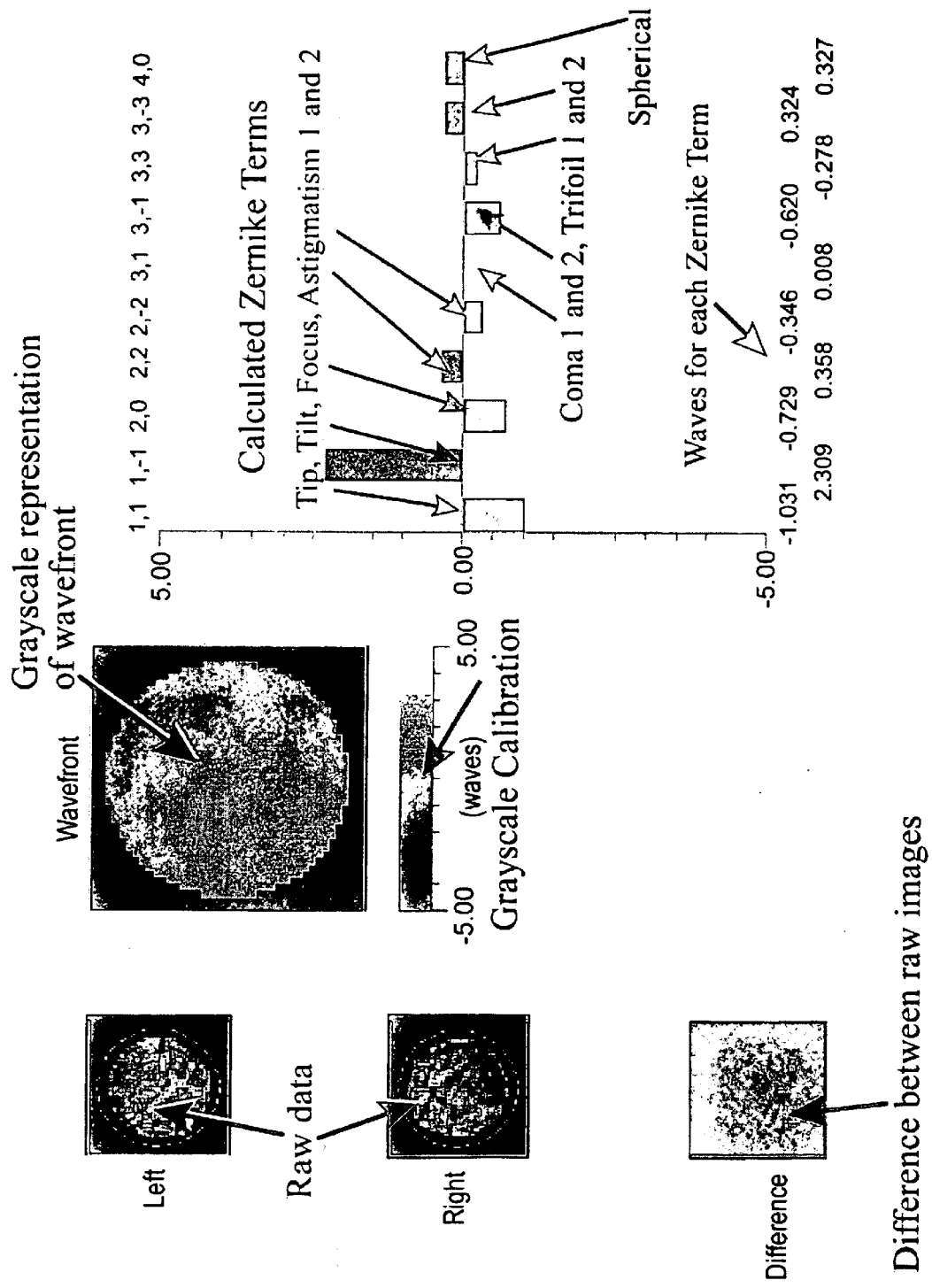
FIG. 6 is a diagram showing the baseline date of the system of FIG. 1, with the container of FIG. 2 filled with Optisol®, but with no cornea.

Next, a baseline for optical system 11, with cornea container 15 located in pupil plane 27 and cavity 57 filled with Optisol® solution, but without a cornea, was established. The baseline data is set forth in FIG. 6. Again, all aberrations can be compensated for or eliminated using the criteria set forth above with regard to FIG. 5.

Figure 7:
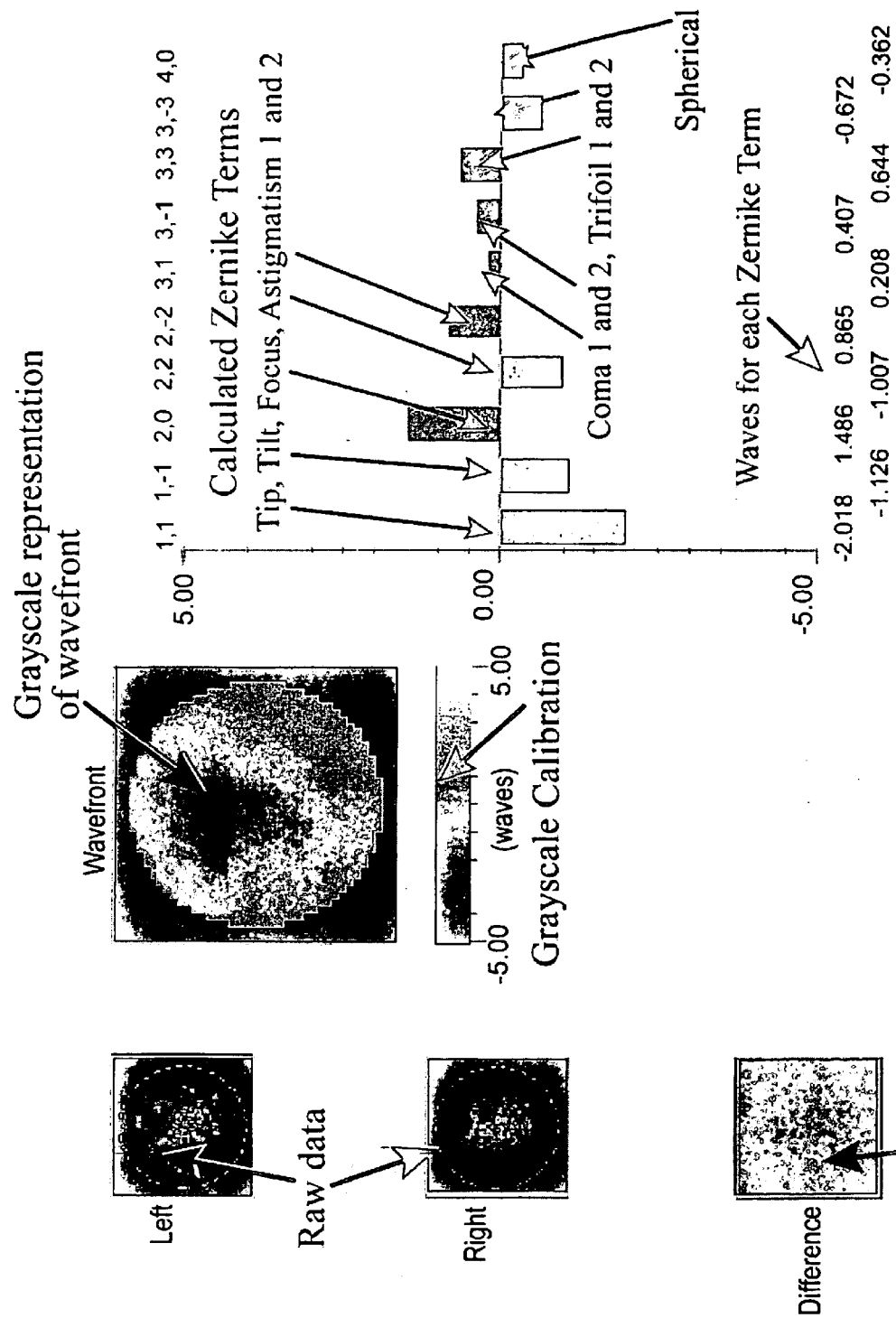
FIG. 7 is a diagram showing the data from an unmodified cornea L, held in the container of FIG. 2, positioned in the pupil plane of FIG. 1, and exposed to coherent and collimated light.

After establishing the baseline, an unmodified donor cornea L was placed in cornea container 15, centered as illustrated in FIG. 2, filled with Optisol® solution, and then closed with optical window 45 in the manner set forth above. Container 15 was then placed in instrument 11, in optical beam path 25 and with cornea L in pupil plane 27, as illustrated in FIG. 1. If necessary, predetermined aberrations can be introduced into the beam path prior to the beam reaching the pupil plane and subsequently accommodated in the analysis of the data. The measured errors are illustrated in FIG. 7. In this figure the tip and tilt terms are irrelevant since they are associated with cornea container 15 and, the orientation of cornea L therein. Cornea L is seen to have focus and astigmatism errors.

Figure 8:
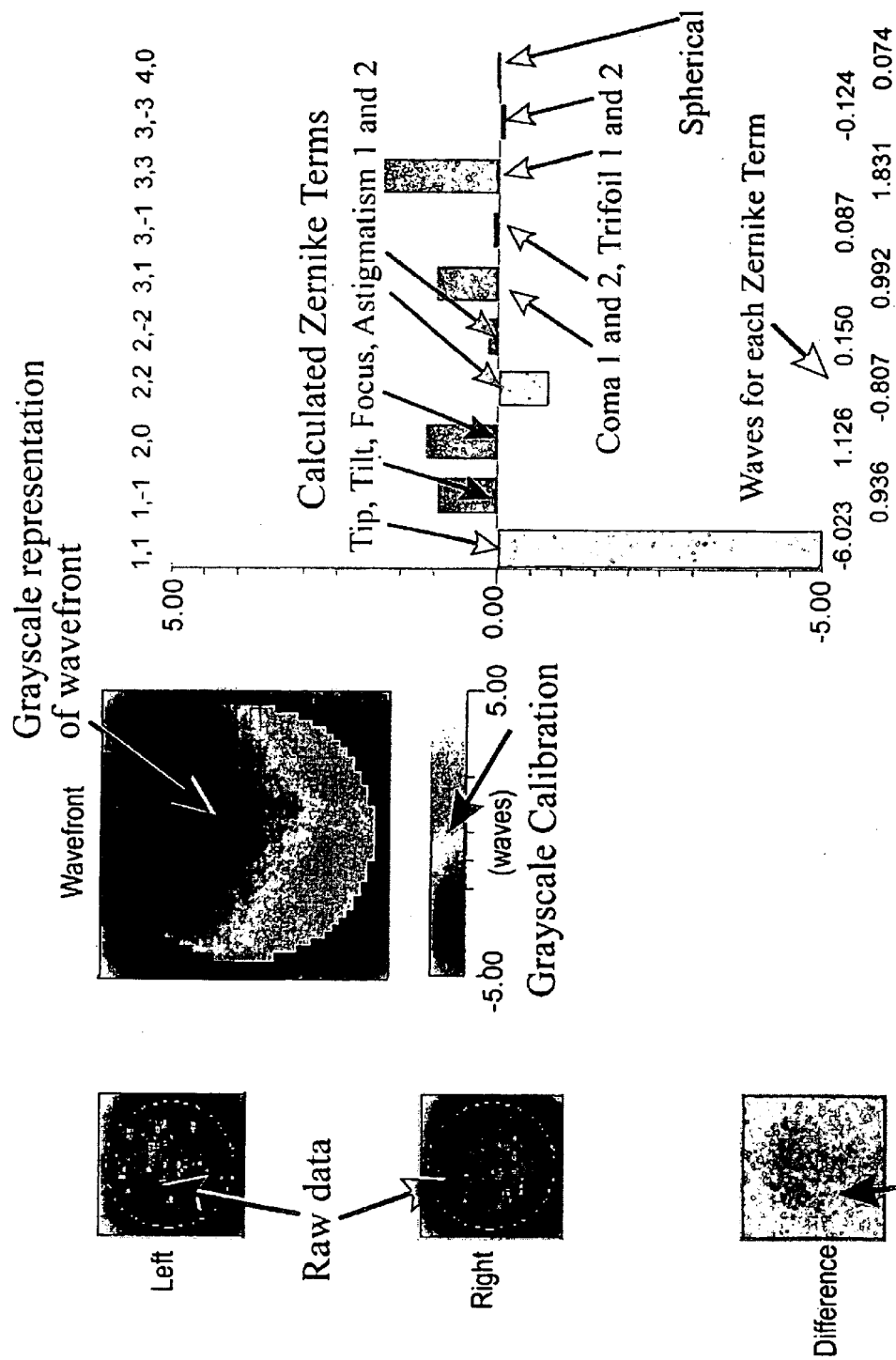
FIG. 8 is a diagram showing the data from a an unmodified cornea R, held in the container of FIG. 2, positioned in the pupil plane of FIG. 1, and exposed to coherent and collimated light.

As with cornea L, cornea R was placed in container 15, and centered as set forth above. Cavity 57 as was then filled with Optisol® and closed with optical window 45. Cornea container 15 was then placed in the pupil plane of instrument 11. The measured errors are illustrated in FIG. 8. As with cornea L, the tip and tilt terms for cornea R are irrelevant since they are associated with container 15 and the specific orientation of cornea R therein, both of which are not controlled. As is evident from FIG. 8, cornea R has focus, astigmatism and coma errors.

The data illustrated in FIGS. 7 and 8 were collected using a 12 mm diameter collimated beam. The measurements were repeated with an 8 mm, and 5 mm collimated beams to see if the measured aberrations were being effected by the irregular outer edge of the corneas. The effect of reducing the beam size was to improve the quality of the images but at the expense of brightness and the area examined. All data were collected with the beam centered on the cornea.

To demonstrate the ability of apparatus 11 to detect surgically modified corneas, cornea L was then modified using a PRK procedure to add 4 diopters of focus change. Cornea R was also subjected to the same procedure to add 8 diopters of focus change. After modification each cornea was, in turn, again centered in cavity 57, which was filled with Optisol® and closed, and container 15 placed in apparatus 11 with the modified cornea again in pupil plane 27.

Figure 9:
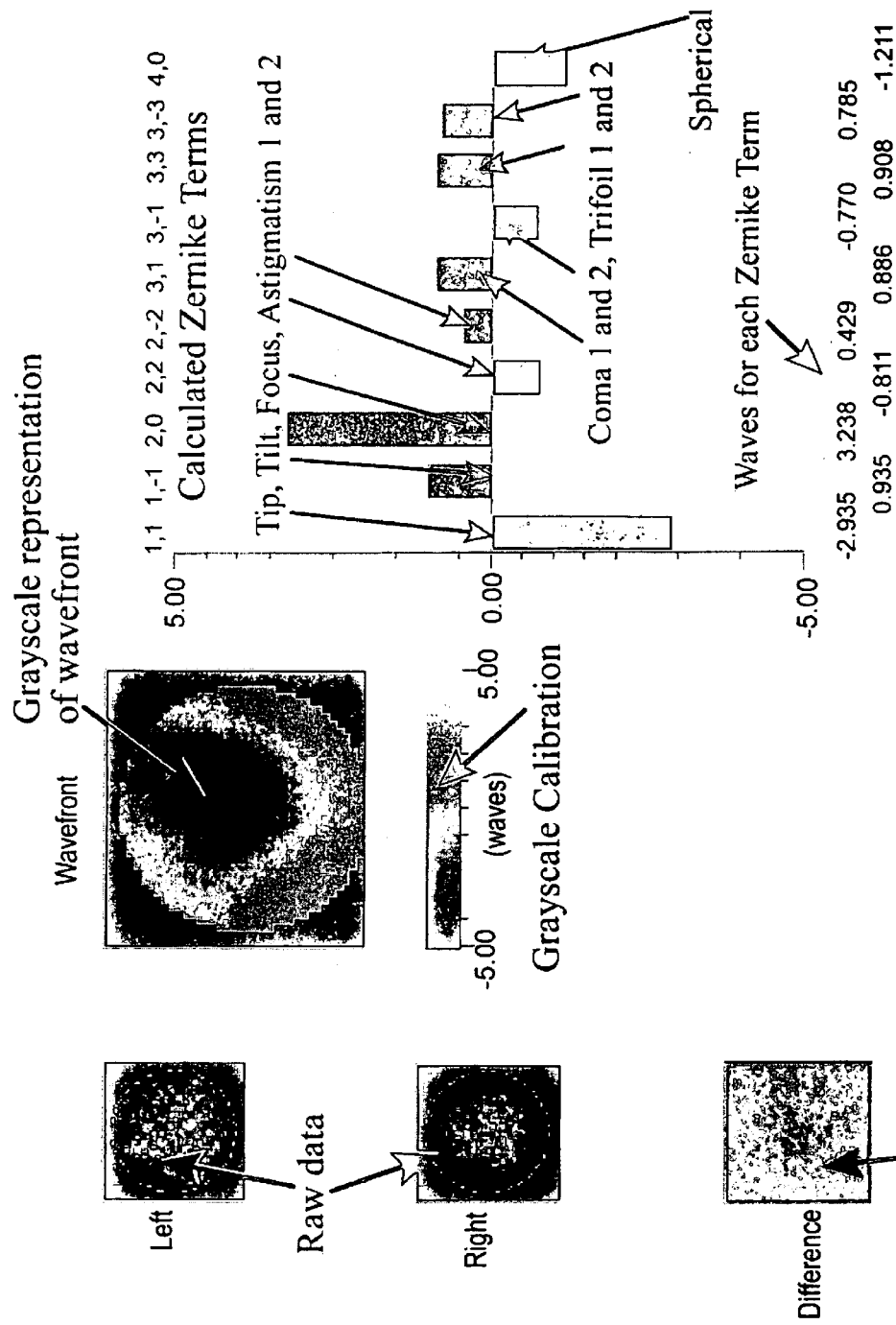
FIG. 9 is a diagram showing the data from cornea L after it has been surgically modified, again held in the container of FIG. 2, positioned in the pupil plane of the system of FIG. 1, and exposed to the same coherent and collimated light.

The measured errors for cornea L (modified) are illustrated in FIG. 9. Again, tip and tilt are irrelevant since they are associated with cornea container 15 and the orientation of cornea L (modified) therein. Cornea L (modified) is seen to have considerably larger focus and astymatism errors then cornea L. The higher order errors (coma 1, coma 2, trifoil 1, trifoil 2 and spherical) are also considerably larger and provide one of the basis for the determination that the cornea has been altered.

Figure 10:
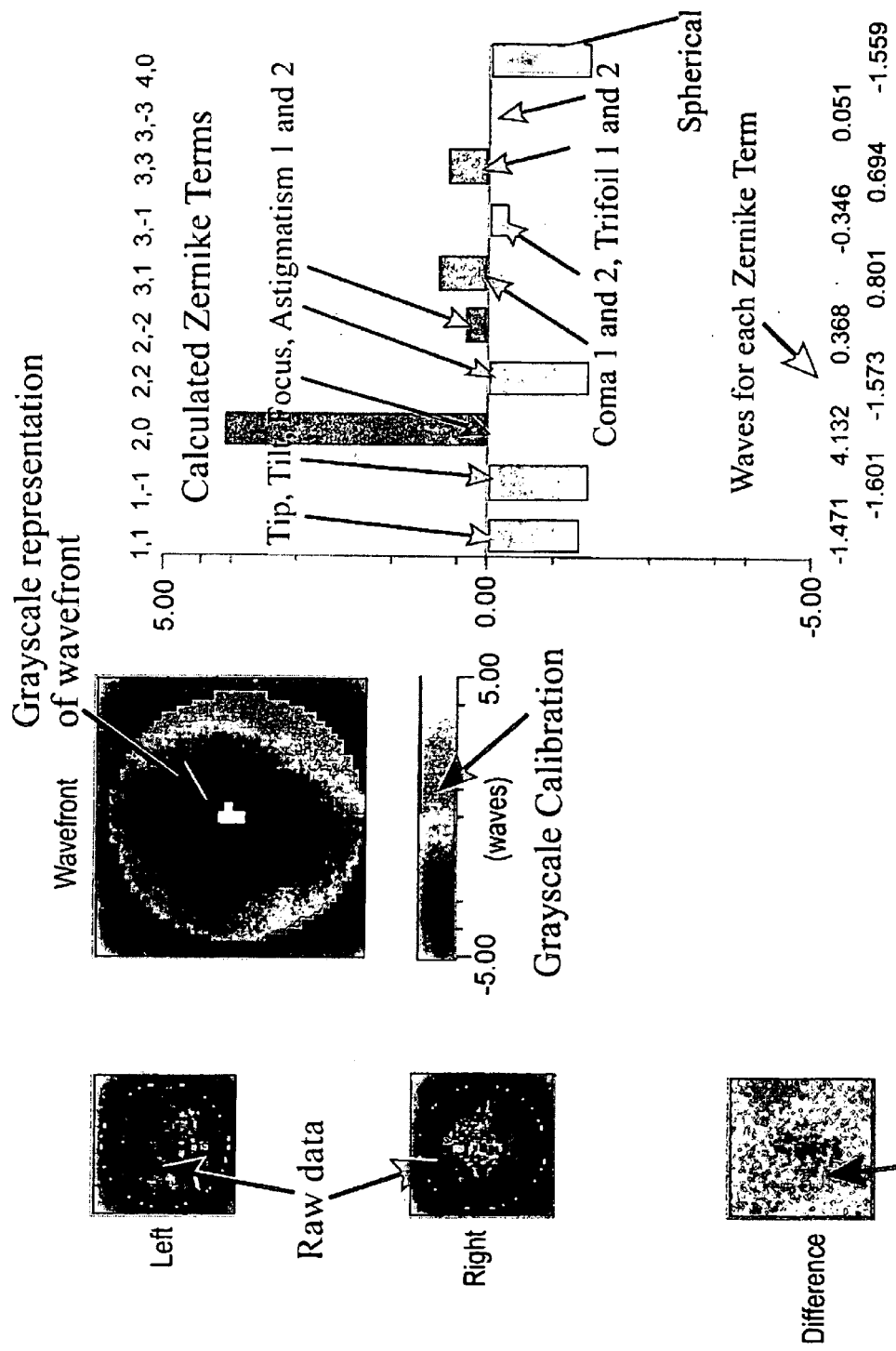
FIG. 10 is a diagram showing the data from the cornea R after it has been surgically modified, again held in the container of FIG. 2, positioned in the pupil plane of FIG. 1, and exposed to the same coherent and collimated light.

The measured errors for cornea R (modified) are illustrated in FIG. 10. As before, tip and tilt are irrelevant. Cornea R (modified) is seen to have considerably larger focus and astymatism errors than cornea R. As with cornea L (modified) the higher order aberrations have also increased (again indicating that the cornea has been modified). A summary of the results is shown in Table 1. Note that the measured difference (in waves) between the two corneas is a factor of 2, the same amount of focus difference introduced by the PRK procedure.

TABLE 1

| Cornea | Focus Term Before Modification (waves) | Focus Term After Modification (waves) | Difference (waves) |
|---|---|---|---|
| L | 1.77 | 3.23 | 1.46 |
| R | 1.024 | 4.132 | 3.108 |

Figure 11:
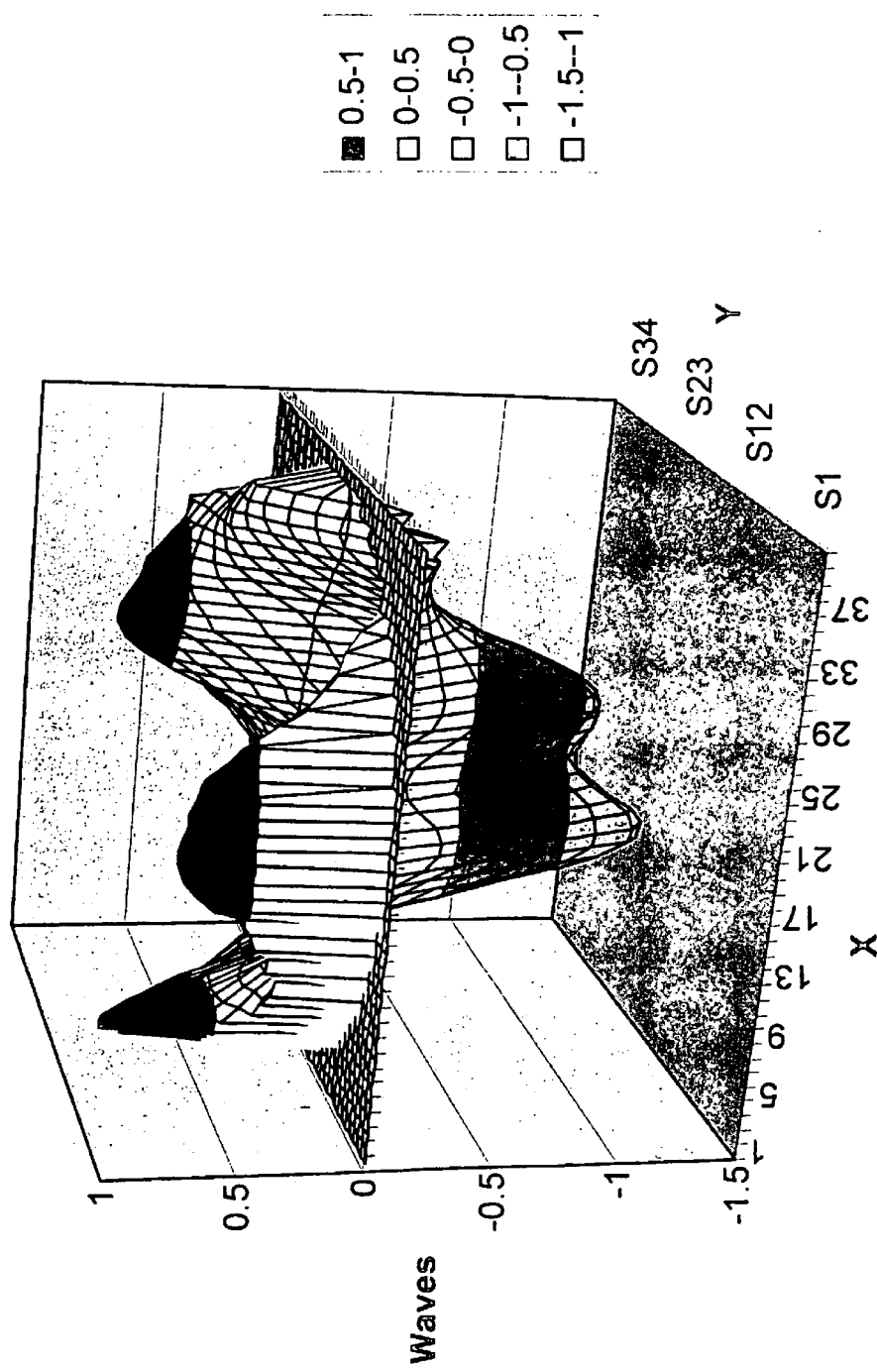
FIG. 11 is a three dimensional presentation of the data set forth in FIG. 7.
Figure 12:
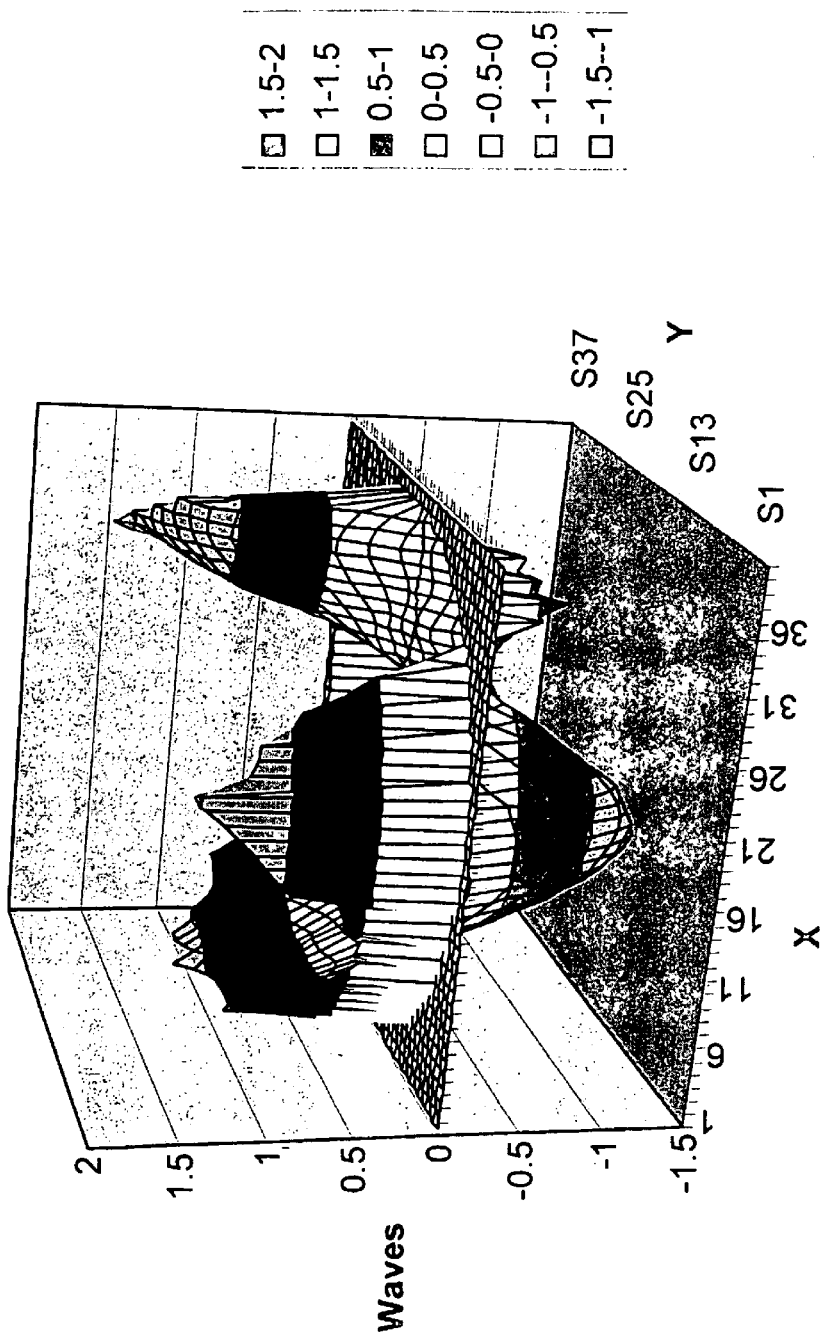
FIG. 12 is a three dimensional presentation of the data set forth in FIG. 8.
Figure 13:
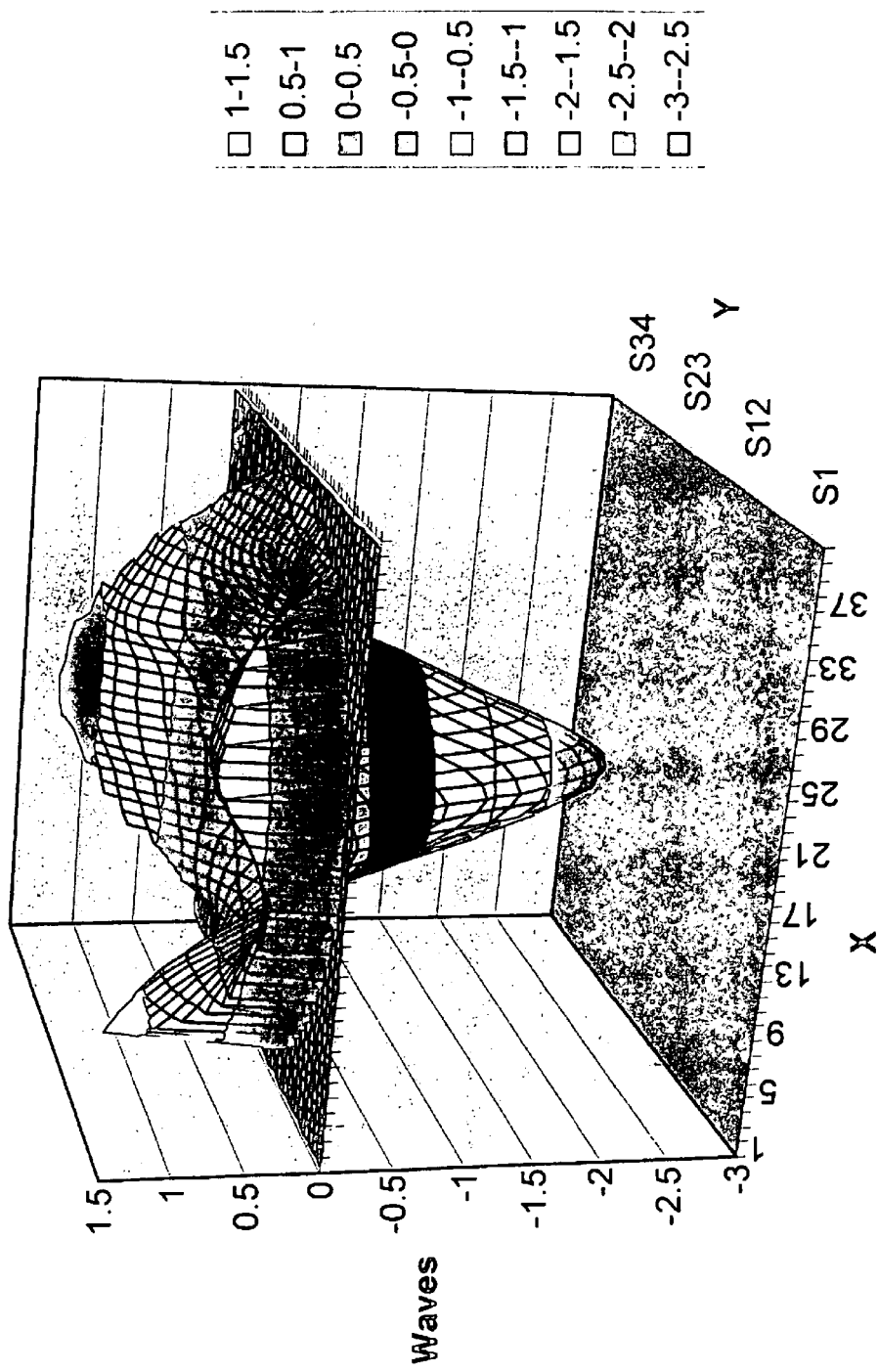
FIG. 13 is a three dimensional presentation of the data set forth in FIG. 9.
Figure 14:
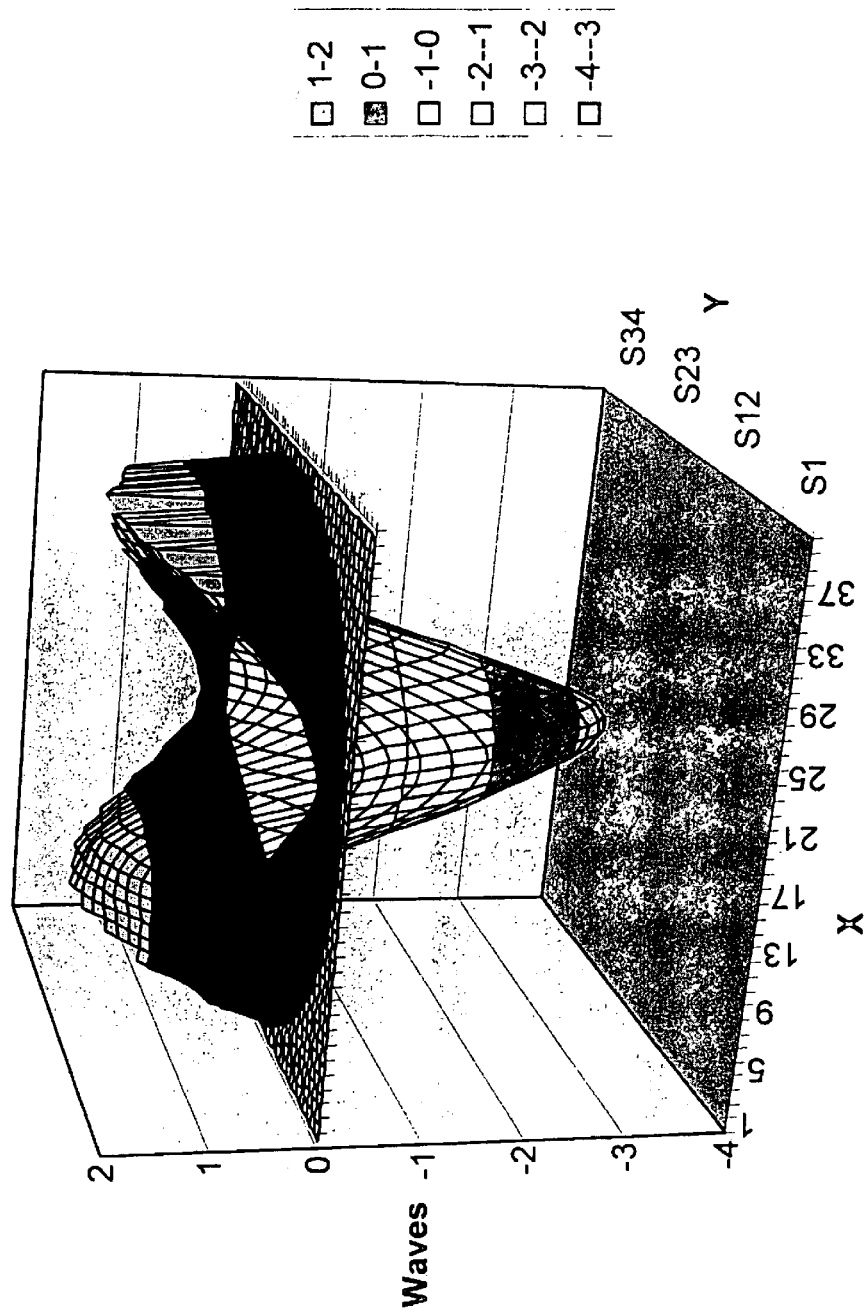
FIG. 14 is a three dimensional presentation of the data set forth in FIG. 10.

An alternative way of illustrating the data set forth in conjunction with FIGS. 7–10 is to present the distorted wavefronts produced by the respective unaltered and altered corneas as three dimensional images. This type of presentation is illustrated in FIGS. 11–14, wherein: FIG. 11 corresponds to FIG. 7; FIG. 12, to FIG. 8; FIG. 13, to FIG. 9; and FIG. 14, to FIG. 10. In FIGS. 11–16, the grey scale on the right is a representation of the distortion. Note the similarities of the Gaussian-like slope of the wavefront aberrations measured for the modified corneas, which provides another basis for determining whether a cornea has been modified.

Figure 15:
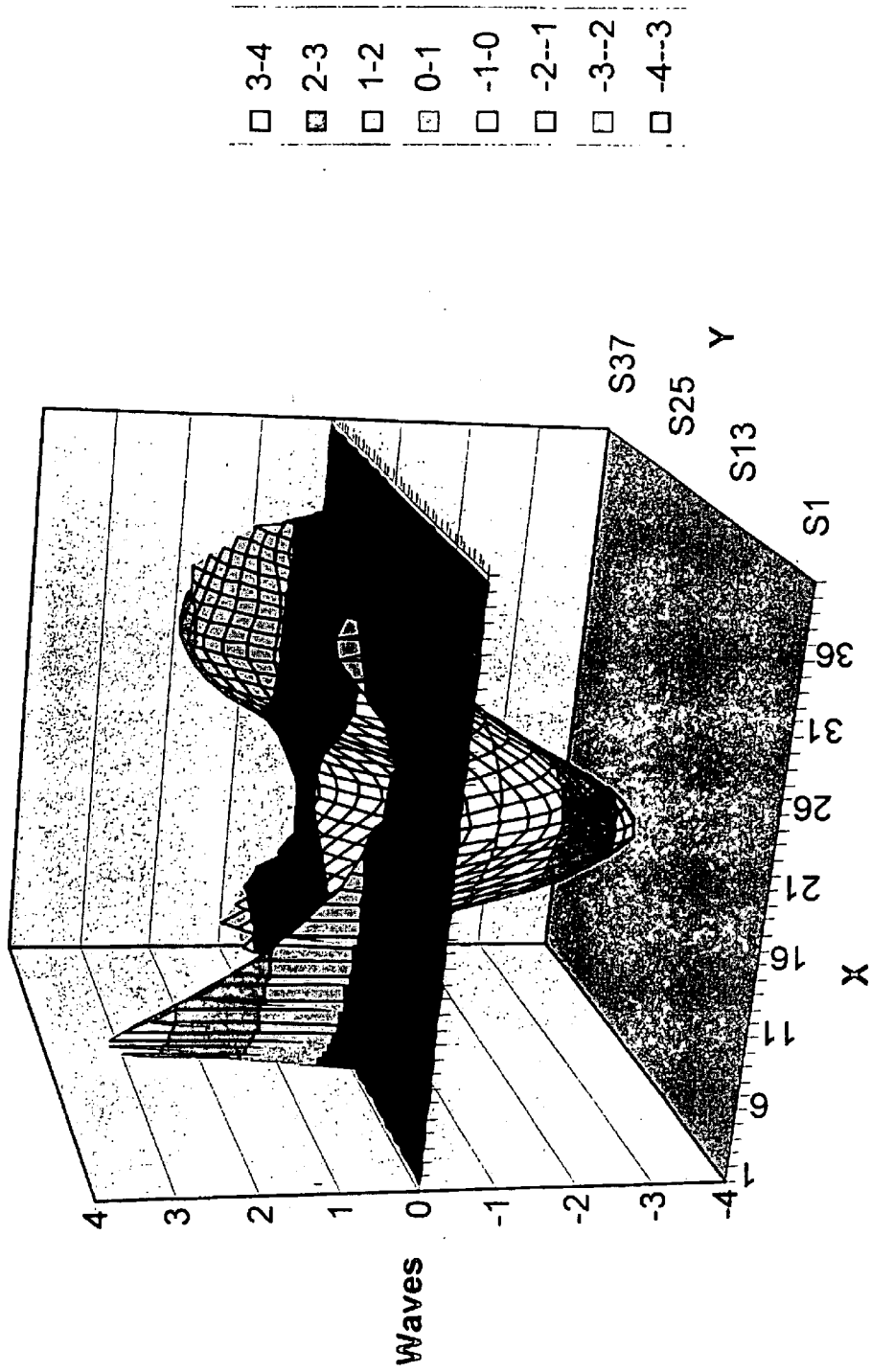
FIG. 15 is a three dimensional presentation of the wavefront of cornea LL which was modified by a LASIK procedure (prior to the death of the donor), held in the container of FIG. 2, positioned in the pupil plane of FIG. 1, and exposed to coherent, illuminated light.
Figure 16:
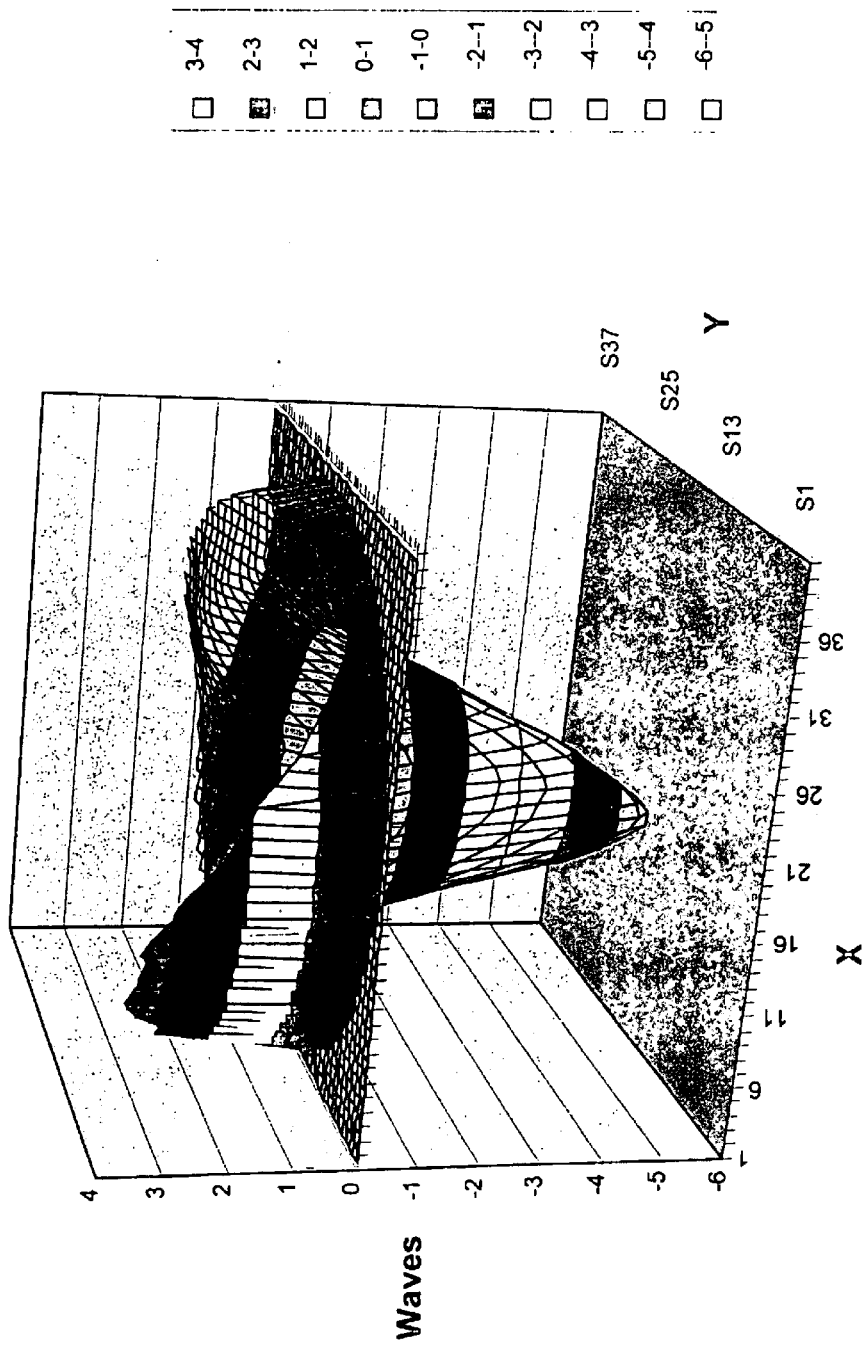
FIG. 16 is a three dimensional presentation of the wavefront of cornea LR which was modified by a LASIK procedure (prior to the death of the donor), held in the container of FIG. 2, positioned in the pupil plane of FIG. 1, and exposed to coherent, illuminated light.

Right (RL) and left (LL) corneas from a donor who had the LASIK corrective surgery prior to death were measured in the same manner as the unmodified corneas L and R (FIGS. 7 and 8) and the PRK modified corneas (FIGS. 9 and 10). FIG. 15 is the left (LL) LASIK modified cornea. FIG. 16 is the right (RL) LASIK modified cornea. The characteristic Gausian-like shape of the wavefront produced by the laser surgery is clearly present in both corneas. As with the PRK modified corneas (FIGS. 9 and 10), the higher order aberrations are considerably larger than those aberrations in the unmodified corneas (FIG. 7 and 8).

The basis for extracting the wavefront from the data collected from detector 21 is to solve the Intensity Transport Equation (I.T.E.). The I.T.E. is derived by expressing the parabolic wave equation for complex amplitude in terms of intensity (I) and phase (Ø), and relates to the rate of change of intensity in the direction of the propagation to the transverse gradient and La Placian of the phase:

$$-\frac{2\pi}{\lambda}\frac{\partial I}{\partial z} = I\nabla^2 \varphi + \nabla I \cdot \nabla \phi$$

For a uniformly illuminate aperture, R, with perimeter P, the ITE simplifies to $$\frac{2\pi}{\lambda}\frac{1}{I_o}\frac{\partial I}{\partial z} = W_R \nabla^2 \varphi - \delta_P \frac{\partial \phi}{\partial \eta}$$

where $W_R$ is the aperture function (=1 inside R, =0 outside R), $\delta_P$ is a delta-function around P, and $\partial\phi/\partial\eta$ is the normal derivative of Ø on P.

Consider the problem of finding the phase at a particular point r. We can express this in terms of an integral involving a delta-function as follows:

$$\phi(r) = \int_R \phi(r')\delta(r-r')$$

If we have a Green's function satisfying $$\nabla^2 G(r, r') = \delta(r - r'), \quad \frac{\partial G(r, r')}{\partial \eta}\bigg|_P = 0$$

then we can say $$\phi(r) = \int_R \phi(r')\nabla^2 G(r, r')$$

Applying Green's $2^{nd}$ identify;

$$\phi(r) = \int_R G(r,r')\nabla^2 \phi(r') + \oint_P \phi(r')\frac{\partial G(r,r')}{\partial \eta} - \oint_P G(r,r')\frac{\partial \phi(r')}{\partial \eta}$$

and the boundary condition on the Green's function;

$$\phi(r) = \int_R G(r,r')\nabla^2 \phi(r') - \oint_P G(r,r')\frac{\partial \phi(r')}{\partial \eta}$$
$$= \int_R G(r,r')\left(\nabla^2 \phi(r') - \delta_P \frac{\partial \phi(r')}{\partial \eta}\right)$$

we get the solution. The term in parenthesis is the right hand side of the ITE. The wavefront phase is thus obtained by measuring the intensity derivative (the left hand side of the ITE), multiplying by the Green's function and integrating;

$$\phi(r) = -\frac{2\pi}{\lambda}\frac{1}{I_o}\int_R G(r,r')\frac{\partial I(r')}{\partial z}$$

The intensity derivative, $$\frac{\partial I(r')}{\partial z}$$

is obtained by the subtraction of two pixellated images. The Green's function is be pre-calculated on the appropriate grid and the solution obtained by the matrix multiplication:

$$\phi = -\frac{2\pi}{\lambda}\frac{1}{I_o}\sum_J Gi,j\left(\frac{\partial I}{\partial z}\right)_j$$

The particular solution will vary, depending on the specifics of the optical design, the detector and the distorted crating used.

Figure 17:
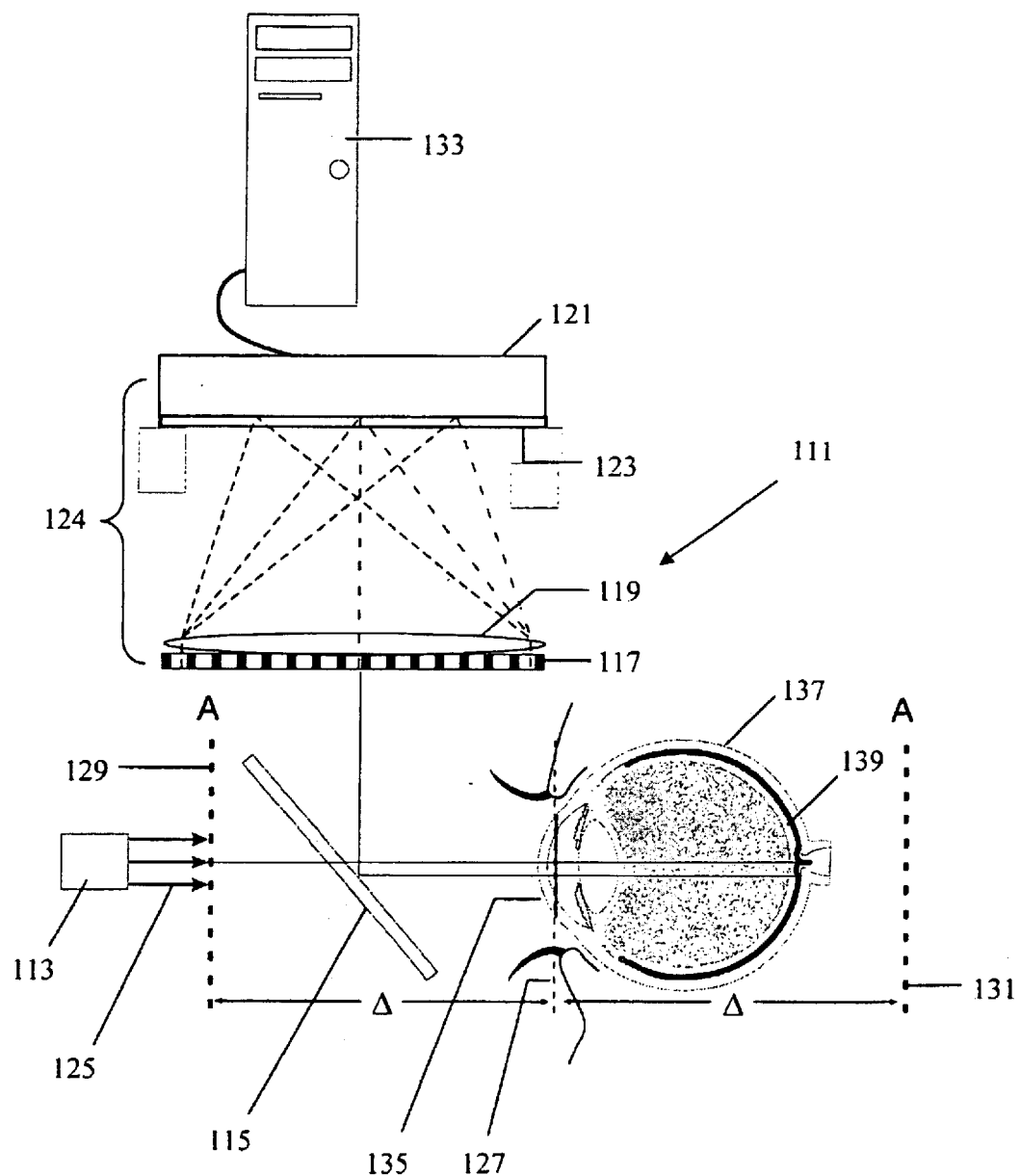
FIG. 17 is a schematic of the optical system used to characterize in vivo corneas.

While the foregoing has dealt with donor corneas, the same basic procedure can also be used on in vivo corneas. With reference to FIG. 17, system 111 includes a source of collimated coherent light 113, a beam splitter 115, a distorted diffraction grating 117, a high quality imaging lens or lens set 119. and a detector 121 (either film or electronic) having a detector plane 123. As with instrument 11, grating 117, lens 119 and detector 121 constitute wavefront sensor 124. System 111 also includes a beam path 125, a pupil plane 127, a first virtual plane 129, a second virtual plane 131, and a computer 133 connected to detector 121 by a data acquisition device, such as a frame grabber located within the computer housing. As with the first embodiment, source 113 is a coherent laser whose energy, when projected into the eye meets FDA approved eye safe levels. Grating 117, which is also distorted according to the grating equation set forth above, is in close proximity with or touching lens 119. System 111 also includes apparatus, not shown, for positioning the patient's head such that his/her cornea is in pupil plane 127.

In operation the beam from source 113 is directed through beam splitter 115, through the cornea 135 and of eye 137, onto the retina 139 where it is reflected back through the cornea and then directed, by beam splitter 115 to wavefront sensor 124. As with instrument 11, the 0, +1 and −1 diffraction orders of grating 117 image pupil plane 127, virtual object plane 129 and virtual object plane 131 onto detector plane 123. Again, the higher order diffraction orders are cut off by an appropriately placed field stop so as not to contaminate the image of the 0 and +1 and −1 orders. Further, with zero order being an image of the pupil plane 127, the images in the +1 and −1 diffraction orders correspond to virtual image planes equidistant from and opposite sides of pupil plane 127. Computer 133 stores the images from detector 121, determines the wavefront from the stored images in the manner set forth above with the I.T.E. and a Green's function, and then analyzes the wavefront for the characteristics that identify an altered cornea (e.g., compares the wavefront to a stored norm).

Whereas the drawings and accompanying description have shown and described the preferred embodiment of the present invention, it should be apparent to those skilled in the art that various chances may be made in the form of the invention without affecting the scope thereof.

We claim:

1. A method of determining whether an in-vivo cornea has been surgically modified, said method including the steps of:
    a. passing a beam of collimated light through said in-vivo cornea twice to produce a wavefront modified by said cornea;
    b. measuring said modified wavefront; and
    c. analyzing said measured, modified wavefront for features that identify the presence of a corneal indicative of surgical modification.

2. The method of claim 1, wherein said analysis is for the presence of higher order optical aberrations.

3. The method of claim 2, wherein said analysis is for the presence of residual grating-like optical aberrations, said optical aberrations being indicative of surgical modification.

4. The method of claim 1, wherein said analysis is for the presence of Gausian characteristics which are indicative of surgical modification.

5. The method of claim 1, wherein said step for passing said beam of collimated light is accomplished with coherent light.

6. The method of claim 1, wherein said step for passing said beam of collimated light is accomplished with incoherent light.

7. The method of claim 1, wherein said step of measuring includes mathematically producing a representation of said modified wavefront.

8. The method of claim 7, wherein measuring includes use of the Intensity Transport Equation and a Green's Function.

9. The method of claim 1 wherein said analysis includes comparing said modified wavefront to a stored wavefront.

10. Method of determining whether or not an in-vivo cornea has been altered, said method including the steps of:
    a. Positioning a person's head such that said in-vivo cornea is in the pupil plane of an optical system;
    b. passing a collimated beam of light through said in-vivo cornea twice and a distorted grating to produce, in the image plane of said optical system, an image of said pupil plane and two virtual image planes located on either side of said pupil plane;
    c. determining from said image, the wavefront of said light after it has passed twice through, and been modified by, said in-vivo cornea; and
    d. analyzing said modified wavefront for features that identify an altered in-vivo cornea.

11. The method as set forth in claim 10, of wherein said intensity maps are the zero, +1 and −1 diffraction orders produced by said distorted grating.

12. The method as set forth in claim 11, wherein said analysis includes the step of comparing said modified wavefront with a stored norm.

13. The method as set forth in claim 11, wherein said modified wavefront is determined from said image, the Intensity Transport Equation and a Green's function.

14. The method of claim 13, wherein said analysis of said modified wavefront is to determine the presence of higher order aberrations.

15. The method of claim 14, wherein said analysis of said modified wavefront is to determine the presence of grating like features which are indicative of a particular type of surgical modification.

16. The method of claim 13, wherein said analysis of said modified wavefront is to determine the presence of Gausian characteristics which are indicative of modifications.

17. The method of claim 10, further including the step of introducing predetermined modifications into said collimated beam of light prior to said beam of light passing through said in-vivo cornea to increase the dynamic range of said determination.

18. The method as set forth in claim 11, wherein said virtual image planes are equally spaced from said pupil plane.

19. Apparatus for determining whether an in-vivo cornea has an abnormality, said apparatus comprising:
  a. a source of collimated light having known wavefront characteristics;
  b. an optical system including an optical path, a distorted grating and lens means, said optical system also including pupil plane, first and second virtual planes, and an image plane, said first and second virtual planes being on opposite sides of and equally spaced from said pupil plane;
  c. means for positioning a person's head such that said in-vivo cornea is in said pupil plane;
  d. means for focusing said virtual planes in said image plane, and means for recording the images of said first and second virtual planes;
  e. means for determining from said images of said first and second virtual planes the wavefront of said source after it has passed twice through and been modified by said in-vivo cornea; and
  f. means for analyzing said modified wavefront for features indicative of an in-vivo cornea with an abnormality.

20. The apparatus of claim 19, wherein said means for positioning said in-vivo cornea includes apparatus for positioning a patient's head such that his/her in-vivo cornea is in said pupil plane.

21. The apparatus of claim 19, wherein said means for determining said modified wavefront includes means for producing a mathematical representation of said modified wavefront.

22. The apparatus of claim 21, wherein said means for producing said mathematical representation includes a computer, the Intensity Transport Equation and a Green's Function.

23. The apparatus of claim 22, wherein said means for analyzing said modified wavefront also includes means for storing said images.

24. The apparatus of claim 23, wherein said means for analyzing includes a stored norm.

* * * * *